United States Patent [19]

Olson et al.

[11] 4,287,201

[45] Sep. 1, 1981

[54] ANOVULATORY METHOD AND CHICKEN FEED COMPOSITIONS

[75] Inventors: George Olson, Clinton; Richard L. Tolman, Warren; Roger M. Weppelman, Scotch Plains, all of N.J.

[73] Assignee: Merck & Co., Inc., Rahway, N.J.

[21] Appl. No.: 126,743

[22] Filed: Mar. 3, 1980

[51] Int. Cl.$^3$ .......................................... A61K 31/415
[52] U.S. Cl. ................................. 424/273 R; 548/315
[58] Field of Search ..................... 548/315; 424/273 R

[56] References Cited

U.S. PATENT DOCUMENTS

| | | | |
|---|---|---|---|
| 3,190,802 | 6/1965 | Zeile et al. | 548/315 X |
| 3,202,660 | 8/1965 | Zeile et al. | 548/315 X |
| 3,595,961 | 7/1971 | Stähle et al. | 548/315 X |
| 3,636,219 | 1/1972 | Culik et al. | 548/315 X |
| 3,937,717 | 2/1976 | Stähle et al. | 424/273 X |
| 3,988,345 | 10/1976 | Franzmair | 548/315 |
| 4,213,995 | 7/1980 | Stahle et al. | 548/315 X |
| 4,244,957 | 1/1981 | Ramuz | 548/315 X |

OTHER PUBLICATIONS

Derwent Abstract of German Pat. No. 2,831,190 1/24/80.
Derwent Abstract of Belgian Pat. No. 860,781 5/16/78.
Derwent Abstract of German Pat. No. 2,457,979 6/16/76.
Derwent Abstract of Belgian Pat. No. 842,118 11/22/76.
Derwent Abstract of Dutch Pat. No. 7,507,456 1/6/76.
Derwent Abstract of German Pat. No. 2,505,297 10/9/75.
Derwent Abstract of German Pat. No. 2,259,160 6/6/74.
Derwent Abstract of S. African Pat. No. 62/4210 4/3/63.
Derwent Abstract of Belgian Pat. No. 623,305 4/5/63.

Primary Examiner—Richard A. Schwartz
Attorney, Agent, or Firm—David L. Rose; William H. Nicholson; Mario A. Monaco

[57] ABSTRACT

2-(Substituted phenylimino)imidazolidines delay the onset of egg production in young pullets and inerrupt egg production in mature hens and are useful in producing an artificial molt.

18 Claims, No Drawings

ANOVULATORY METHOD AND CHICKEN FEED COMPOSITIONS

BACKGROUND OF THE INVENTION

This invention is concerned with novel compounds and other related compounds of general structural formula:

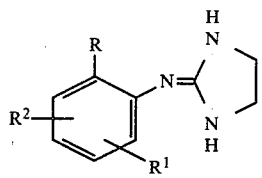

and a method of delaying the onset of egg production in young pullets and interrupting the egg production in mature laying hens by administration of one or more of these compounds usually in a feed mix.

Delaying the onset of egg production in the broiler-breeder industry and interrupting the egg production cycle in mature hens in the table egg industry are widely practiced by commercial poultry and egg producers.

The onset of production in young pullets is delayed in essentially all commercial broiler-breeder hens to reduce the number of small eggs produced. Egg size is highly correlated with the age of the bird and chick size is highly correlated with egg size. Therefore, by holding replacement pullets out of production for 2 or 3 weeks at the start of the laying cycle, a larger chicken is produced. It has been shown that layers have a genetic potential for producing a certain number of eggs. Therefore, delaying the onset of egg production does not reduce the total number of eggs laid during a production cycle but does increase the number of large eggs produced.

Interrupting the egg production cycle in commercial layers to improve egg shell and interior egg quality and to extend the production span and life of the hen has been a practice in commercial egg production for several decades. The current methods of interrupting egg production (forced molt) are centered around a stress system of withdrawing feed and/or water for varying time intervals depending on the system used. This stress causes the birds to halt egg production, however, it also causes the birds to go into a full molt (lose feathers). The second physiological effect is believed to be unnecessary and therefore a very undesirable side effect. Once the birds are out of production, a nutritional management regime of restricting feed, water or nutrients is put into effect. The most common procedure is to restrict nutrients by substituting a cereal grain for the laying mash which necessitates two dietary changes during the laying pause. All of the procedures currently practiced require very strict management control which utilizes a large amount of labor and is difficult inasmuch as an overly restrictive program will result in an abnormally high incidence of mortality in the layer flock, while a lenient program will result in an undesirably slow cessation in egg production. Also, switching the hens to a grain diet, low in nutrients, does not afford the hen an opportunity to regenerate her body nutrient stores. Regeneration does not take place until the hen is again placed on the high nutrient diet. Within a few days after receiving the adequate diet, the hen resumes egg production and there is inadequate time for her to rebuild body stores.

Surprisingly it has been found that compounds of a class known generically as 2-(substituted phenylimino)imidazolidines, some of which are novel, are anovulatory agents which on administration to young pullets delay the onset of egg production with the benefits inherent therein, and on administration to laying hens cause a reversible interruption in egg production with all the beneficial effects of a traditional forced molt procedure. The novel method described herein has the added advantages of: a reduction in bird mortality; a more uniform cessation of egg production; a more uniform return to full egg production; maintenance of the birds on a nutritionally adequate diet during the production pause; reduction in labor and management costs; and greater flexibility in the timing of the laying interruption.

It is therefore an object of this invention to provide a group of 2-(substituted phenylimino)imidazolidines which are anovulatory agents some of which are novel.

It is also an object of this invention to provide a novel method of mimicking a forced molt in laying hens with all of the advantages and none of the disadvantages inherent therein which comprises the administration of an anovulatory 2-(substituted phenylimino)imidazolidine.

It is a further object of this invention to provide novel compositions for administration of the anovulatory 2-(substituted phenylimino)imidazolidines to laying hens.

Other objects are inherent in the foregoing or will become apparent from the following.

DETAILED DESCRIPTION OF THE INVENTION

The novel compounds of this invention have structural formula:

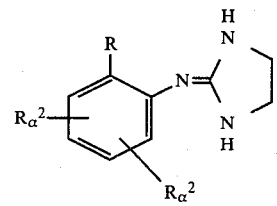

or non-toxic salt thereof, wherein
R is $C_{1-4}$ alkyl, either straight or branched chain such as methyl, ethyl, 1- or 2-propyl, or 1- or 2-butyl, especially methyl; $C_{2-5}$ alkenyl; or halo, such as chloro, bromo or iodo, especially chloro;
$R_\alpha^1$ is hydrogen, $C_{1-4}$ alkyl or halo; and
$R_\alpha^2$ is
(1) $C_{1-4}$ alkanoyl, such as formyl, ethanoyl, or the like,
(2) carboxy,
(3) $C_{1-3}$ alkoxycarbonyl,
(4) $C_{1-4}$ alkylthio,
(5) phenoxy, either unsubstituted or substituted with $C_{1-3}$ alkyl, $C_{1-3}$ alkoxy or halo,
(6) phenylthio, either unsubstituted or substituted with $C_{1-3}$ alkyl, $C_{1-3}$ alkoxy or halo,
(7) $C_{1-4}$ alkyl substituted with
(a) hydroxy,
(b) $C_{1-3}$ alkoxy, or
(c) di($C_{1-3}$ alkyl)amino, (8) C$_{2-5}$ alkenyl, or
(9) di(C$_{1-3}$ alkyl)amino.

In a preferred embodiment of the novel compounds R is C$_{1-4}$ alkyl, especially methyl; R$_\alpha^1$ is hydrogen, and R$_\alpha^2$ is C$_{1-3}$ alkoxy-C$_{1-4}$ alkyl, especially methoxymethyl. In an even more preferred embodiment, R$_\alpha^2$ is in the 3-, or 4-position.

The active anovulatory compounds useful in the novel method of this invention have structural formula:

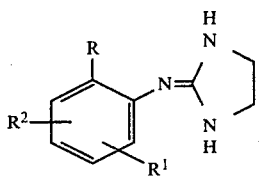

or a non-toxic salt thereof, wherein
R is
(1) C$_{1-4}$ alkyl, either straight or branched chain, such as methyl, ethyl, 1- or 2-propyl, or 1- or 2-butyl, especially methyl,
(2) C$_{2-5}$ alkenyl, or
(3) halo, such as chloro, bromo or iodo, especially chloro;

R$^1$ and R$_2$ are independently
(1) C$_{1-4}$ alkyl, either straight or branched chain, such as methyl, ethyl, 1- or 2-propyl, or 1- or 2-butyl, especially methyl,
(2) C$_{2-5}$ alkenyl, or
(3) halo, such as chloro, fluoro, bromo or iodo, especially chloro,
(4) hydrogen,
(5) nitro,
(6) amino,
(7) C$_{1-3}$ alkylamino,
(8) di(C$_{1-3}$ alkyl)amino,
(9) hydroxy,
(10) carboxy,
(11) C$_{1-3}$ alkoxycarbonyl,
(12) C$_{1-4}$ alkanoyl, such as formyl, ethanoyl or the like,
(13) C$_{1-4}$ alkylthio,
(14) trifluoromethylthio,
(15) phenylthio, either unsubstituted or substituted with C$_{1-3}$ alkyl, C$_{1-3}$ alkoxy, or halo such as chloro, or bromo,
(16) phenoxy, either unsubstituted or substituted with C$_{1-3}$ alkyl, C$_{1-3}$ alkoxy, or halo such as chloro or bromo,
(17) C$_{1-4}$ alkyl substituted with
(a) amino,
(b) C$_{1-3}$ alkylamino,
(c) di(C$_{1-3}$ alkyl)amino,
(d) hydroxy, or
(e) C$_{1-3}$ alkoxy.

It is preferred that R be C$_{1-4}$ alkyl, one of R$^1$ and R$^2$ be hydrogen and the other be C$_{1-4}$ alkyl, fluoro, chloro, or C$_{1-3}$ alkoxy-C$_{1-4}$ alkyl.

It is still more preferred that R be methyl, one of R$^1$ and R$^2$ be hydrogen, and the other be C$_{1-4}$ alkyl.

It is even more preferred that the substituent R$^1$ or R$^2$ that is not hydrogen, be in the 6-position.

Preferred specific anovulatory compounds are:
2-(2,6-dimethylphenylimino)imidazolidine,
2-(3-chloro-2-methylphenylimino)imidazolidine,
2-(6-chloro-2-methylphenylimino)imidazolidine,
2-(2-methyl-4-methoxymethylphenylimino)imidazolidine, or
2-(5-fluoro-2-methylphenylimino)imidazolidine.

Non-toxic salts contemplated to be within the scope of this invention are the hydrochloride, hydrobromide, maleate, tartrate, sulfate, nitrate or the like, preferably the hydrochloride.

The novel method of interrupting egg production comprises the administration of one or more of the foregoing anovulatory agents to a laying hen. The route of administration can be orally or by injection. Obviously, in practice, involving large flocks, the oral route is preferred and then preferably mixed with the feed stuff or included in the drinking water.

For administration by means of incorporation in the drinking water, the anovulatory agent or a water soluble salt thereof, if the free base is not soluble enough, is incorporated at concentrations of about 10 to about 500 parts per million by weight. A preferred range is about 25–100 parts per million and the preferred salt is a hydrochloride salt.

Much more concentrated solutions of about 1 to about 10% by weight are convenient for final dilution to drinking water concentrations. These will normally contain also about 0.01 to about 0.1% by weight of a preservative such as sodium or potassium benzoate, sodium or potassium sorbate, sodium propionate, methyl, ethyl, propyl or butyl paraben, ethanol or propylene glycol.

A feed will typically contain from about 20 to about 500 parts per million (ppm) preferably from about 30 to about 250 ppm of one of the anovulatory agents previously described. The optimum levels will vary with the particular anovulatory agent selected, but is readily determined by one skilled in the art of poultry management.

The novel feed compositions of this invention are prepared by dispersing the anovulatory agent by mechanically mixing it in finely ground form with the poultry feedstuff, or with an intermediate formulation (premix) that is subsequently blended with other components to prepare the final poultry feedstuff that is fed to the poultry. Typical components of poultry feedstuffs include soybean oil meal, corn meal, fish meal, fermentation residues, ground and rolled oats, wheat shorts and middlings, alfalfa and meat scraps, together with mineral supplements such as bone meal and calcium carbonate and vitamins.

Suitable compositions also include feed premixes in which the active ingredient is present in relatively large amounts and which are suitable for addition into the feed either directly or after an intermediate dilution or blending step. Such compositions may also be added to the animals feed in the form of a top dressing. Typical carriers or diluents suitable for such compositions include for example, distillers dried grains such as corn distiller's dried grains and corn distiller's grains, corn meal and corn meal germ, citrus meal, fermentation residues, ground oyster shells, wheat shorts and wheat standard middlings, molasses solubles, corncob meal, edible bean mill feed, soya grits, crushed limestone and the like. The active compound is intimately dispersed throughout the carrier by methods such as grinding, stirring, milling or tumbling. Compositions containing from about 2 to 50% by weight, especially from about 5 to 25% by weight of the anovulatory agents described above are particularly suitable as feed premixes.

Examples of typical feed premixes containing 2-(2,6-dimethylphenylimino)imidazolidine dispersed in a solid inert carrier are:

|   |   | lbs. |
|---|---|---|
| A. | 2-(2,6-Dimethylphenylimino)-imidazolidine | 6.0 |
|   | Wheat standard middlings | 94.0 |
| B. | 2-(2,6-Dimethylphenylimino)-imidazolidine | 10.0 |
|   | Corn distiller's dried grains | 90.0 |
| C. | 2-(2,6-Dimethylphenylimino)-imidazolidine | 20.0 |
|   | Corn germ meal | 30.0 |
|   | Corn distiller's grains | 50.0 |

This invention is not limited to anovulatory compositions having the imidazolidines hereinabove described as the sole active ingredients. Also contemplated within its scope is what might be called "combined treatment" where the anovulatory agent and one or more active agents such as a coccidiostat are administered concurrently. For such purposes, compositions may be prepared containing an anovulatory agent admixed with one or more coccidiostats such as sulfquinoxaline, other sulfa compounds, 4,4'-dinitrocarbanilide-2-hydroxy-4,6-dimethylpyrimidine complex, 3,3'-dinitrodiphenyldisulfide, 5-nitrofurfural semicarbazone, amprolium, zoalene, buquinolate, ethopabate, monensin, 9-(2-chloro-6-fluorobenzyl)adenine and the like.

It will likewise be understood by those skilled in this art that special feed supplement formulations and finished animal feeds containing vitamins, antibiotics, growth-promoting agents and other nutritional substances may include the anovulatory agents active in the method of this invention.

Generally, the process for preparing the novel compounds of this invention comprises the condensation of an appropriately substituted aniline with a 2-halo-2-imidazoline, preferably 2-chloro-2-imidazoline, which is represented as follows:

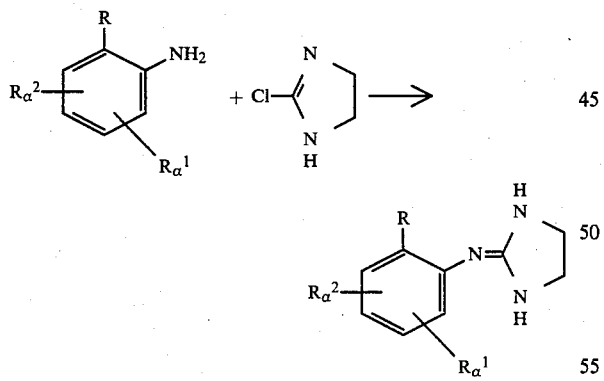

If the foregoing condensation is not the last step in the synthesis of the novel compounds it is nonetheless a key step in the overall synthetic schemes.

The condensation is conducted in a protic solvent such as a $C_{1-4}$ alkanol or water, or mixtures thereof especially mixtures of about equal volumes of methanol and water at a temperature between about $-10°$ C. and about $+30°$ C. until the reaction is substantially complete, usually in about 10 to about 30 hours. The product is conveniently isolated by making the reaction mixture strongly alkaline with an alkali metal hydroxide, especially sodium hydroxide followed by extraction with an immiscible organic solvent such as a polyhaloalkane, especially dichloromethane. Further purification, if necessary, is accomplished by extraction with aqueous acid, and precipitation with alkali or if necessary back-extraction of the aqueous acid with an organic solvent followed by evaporation of the solvent.

The above-described general process is not necessarily the best process, especially wherein $R_\alpha^2$ represents $di(C_{1-3}$ alkyl$)$amino-$C_{1-4}$ alkyl. In this case the preferred process is represented by:

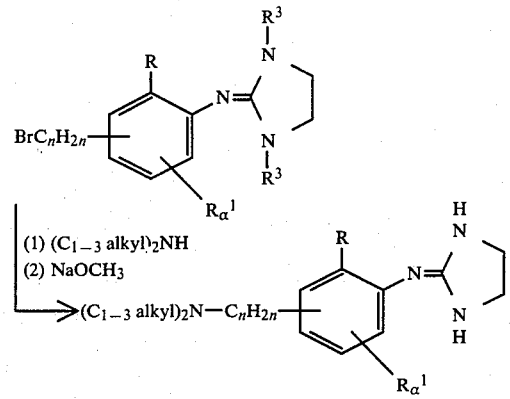

wherein $R^3$ is $C_{2-3}$ alkanoyl and n is 1–4. The reaction between the bromo-alkyl group and the secondary amine proceeds spontaneously in an organic solvent, such as a polyhaloalkane, at or near ambient temperature and is completed in a short period of time. Temperature and time are not critical but ranges of about 0° C. to reflux temperature and about 10 minutes to about 2 hours are reasonable. The $R^3$ groups are readily removed by treating the product of the first reaction with an alcoholic solution of an alkali metal alkoxide, such as methanolic sodium methoxide for about 15 minutes to about 2 hours at a temperature from about 0° C. to about reflux temperature.

The same starting material on treatment with a base such as an alkali metal carbonate or alkali metal $C_{1-3}$ alkoxide, wherein the alkali metal is sodium or potassium, in a $C_{1-3}$ alkanol as solvent, provides an alkoxyalkylphenyliminoimidazolidine in accordance with the following reaction:

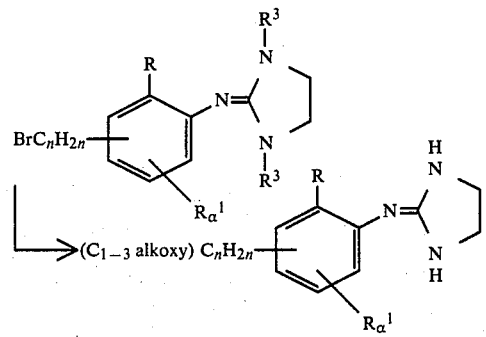

Where $R_\alpha^2$ is hydroxy-$C_{1-4}$ alkyl, the compounds are prepared by reduction of a $C_{1-4}$ alkanoyl group with a complex metal hydride such as sodium borohydride in dilute $C_{1-3}$ alkanolic sodium or potassium hydroxide at about 20° C. to about reflux temperature for about 3 to about 12 hours, preferably about 4-8 hours, as shown in the following reaction scheme:

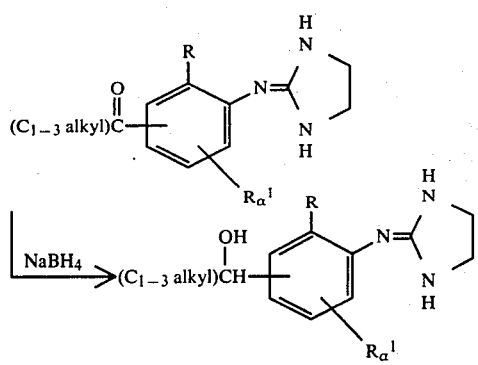

Where $R_\alpha^2$ is hydroxy, the compounds are generally prepared by de-etherification of a corresponding alkoxy compound by treatment with 48% hydrobromic acid at about 50° C. to about reflux temperature for 3 to about 12 hours, preferably about 4 to about 8 hours in accordance with the following reaction scheme:

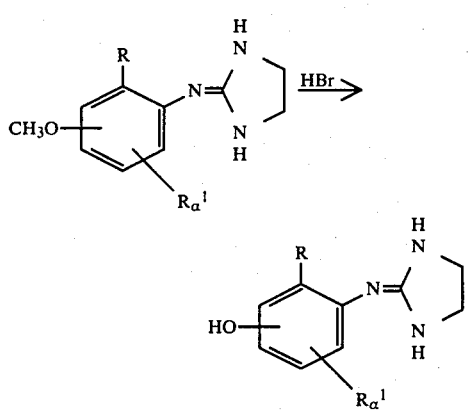

Those compounds wherein $R_\alpha^2$ is carboxy are generally prepared by deesterification of the corresponding esters with a dilute strong aqueous acid such as hydrochloric, sulfuric, hydrobromic, trifluoroacetic, trichloroacetic, nitric or the like by heating at about 50° C. to reflux temperature for 10-24 hours, preferably for about 16-20 hours, as represented below:

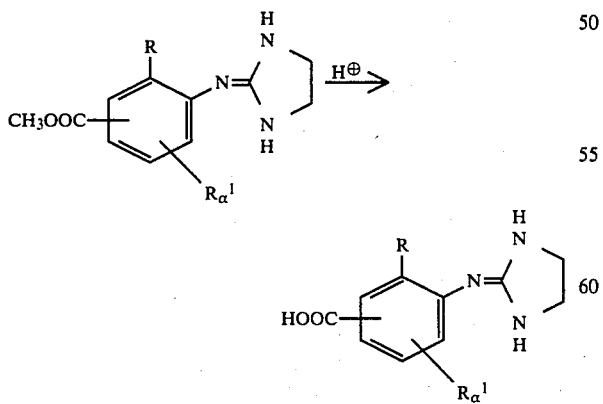

In the special instance in which R and $R_\alpha^1$ represent 2,6-dimethyl, the 4-COOH group can be formed by direct oxidation of a 4-CH$_3$ group by treating the 2,4,6-trimethyl compound with chromium trioxide in acetic acid at about 25° C. to about 100° C. for 2 to about 8 hours, preferably at about 40° C. to about 60° C. for 3 to about 5 hours. This oxidation is also accomplished with potassium dichromate in sulfuric acid.

Novel compounds carrying a dialkylamino group may be prepared by reductive alkylation of the corresponding nitro compound in which the imidazolidine nitrogens are protected preferably with an alkanoyl group, followed by removal of the protecting groups. The process is as shown in the following scheme:

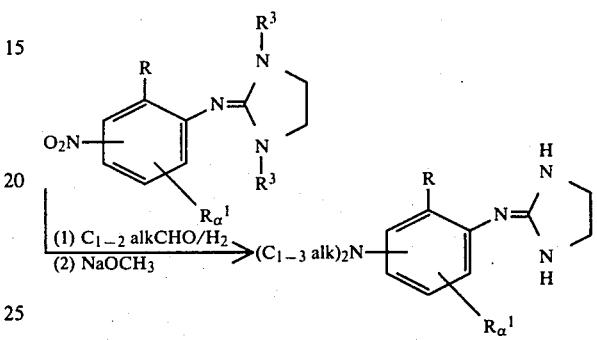

The reductive alkylation is performed by treating the nitro compound with an aldehyde of formula $C_{1-2}$ alkyl—CHO and a noble metal catalyst such as platinum oxide in a lower alkanol such as methanol, ethanol or propanol and agitating under a hydrogen atmosphere at atmospheric pressure or slightly above, at ambient temperature until hydrogen uptake ceases. The alkanoyl protective groups ($R^3$) are removed by treatment with a catalytic amount of sodium methoxide in methanol at ambient temperature.

Novel compounds wherein $R_\alpha^2$ is $C_{2-5}$ alkenyl may be prepared by treatment of the corresponding formyl compound in which the imidazolidine nitrogens are protected with an appropriate Wittig reagent, followed by removal of the nitrogen protecting groups:

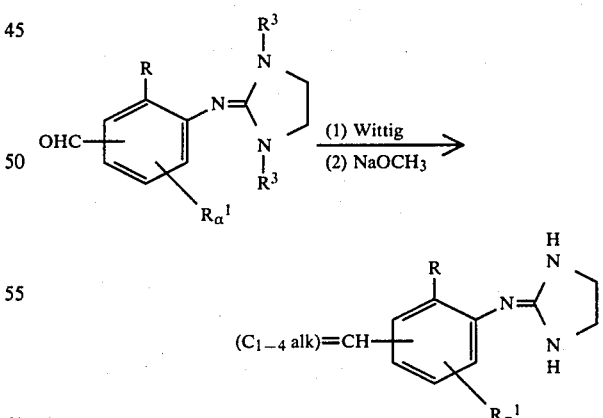

The Wittig reaction is conducted under standard conditions in dimethyl sulfoxide at ambient temperature over about 12 to 24 hours. The $R^3$ groups are removed in the usual manner.

Novel compounds carrying an alkenyl group may also be prepared by dehydration of an hydroxyalkyl group as follows:

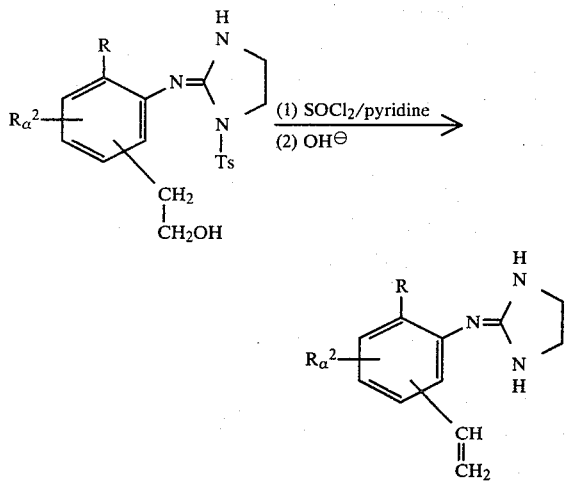

The hydroxyethyl compound is treated with a mixture of pyridine and thionyl chloride at a temperature from about 50° C. to about reflux temperature for about 1 to about 6 hours, preferably about 3 hours. The resulting alkenyl compound carrying the N-Tosyl group is then treated with strong alkali solution or optimally with metallic sodium in liquid ammonia.

EXAMPLE 1

2-(4-Chloro-2-methylphenylimino)imidazolidine

A solution of 6.84 g (48 mmoles) of 4-chloro-2-toluidine in 15 ml of methanol is added rapidly to a solution of 4.04 g (20 mmoles) of 2-chloro-2-imidazoline bisulfate in 40 ml of methanol and 8 ml of water. A precipitate forms and the mixture becomes warm. It is stirred overnight at ambient temperature.

The mixture is diluted with 100 ml of ice cold water and made strongly alkaline with sodium hydroxide in the presence of dichloromethane. The layers are separated and the aqueous phase is extracted twice more with dichloromethane. The combined extracts are washed with water and saturated sodium chloride. The solution is then extracted with 2×20 ml of 2 N acetic acid and once with saturated sodium chloride.

The extracts are combined, washed with dichloromethane and ether and then concentrated to remove organic solvents. The solution is stirred while 50% sodium hydroxide solution is added slowly. At the first permanent cloudiness it is seeded and scratched to start crystallization. Additional sodium hydroxide solution is added until there is no more precipitation. The product is filtered, washed well with water and with hexane and dried under vacuum to give 2.56 g of 2-(4-chloro-2-methylphenylimino)imidazolidine (61%), m.p. 137°–138° C.

EXAMPLE 2

2-(2-Chlorophenylimino)imidazolidine

To 2-chloroimidazoline bisulfate (60.0 g, 300 mmoles) in methanol (600 ml) and water (150 ml) is added with stirring 2-chloroaniline (81.1 g, 67 ml, 636 mmoles). The heterogeneous mixture is stirred at ambient temperature overnight. After 20 hours the mixture is poured into ice water, made strongly alkaline with sodium hydroxide and extracted with dichloromethane twice. The organic extracts are washed once with water and once with saturated sodium chloride solution and then extracted with 2 N acetic acid (2×1 liter). The combined acid extracts are backwashed with dichloromethane, made strongly alkaline with sodium hydroxide, and once again extracted with dichloromethane twice. The dichloromethane extracts are combined, washed with water and then sodium chloride solution and finally dried and evaporated in vacuo. The solid residue (31 g) is dissolved in hot toluene, filtered, and diluted with hexane (total volume 3 liters). Colorless crystals separate which are filtered, washed with hexane and air-dried, to give 28.2 g of 2-(2-chlorophenylimino)imidazolidine, m.p. 133°–134° C.

EXAMPLE 3

2-(5-Acetyl-2-methylphenylimino)imidazolidine

Step A: Preparation of 4-methyl-3-nitroacetophenone

To 250 ml of cold (−20° C.) concentrated sulfuric acid is added with stirring 4-methylacetophenone (40 g, 300 mmoles). When the first addition is complete, a mixture of 25.5 ml (36.3 g, 300 mmoles) of 70% nitric acid and 300 g of 20% fuming sulfuric acid is added dropwise over 40 minutes. The temperature remains below −15° C. The mixture is stirred for an additional 30 minutes and then poured onto ice. The solids are filtered, washed with water and then with hexane. The solids are dissolved in dichloromethane and washed with 10% sodium bicarbonate solution and finally with saturated sodium chloride solution. The organic phase is dried, charcoaled, concentrated and diluted with hexane, whereupon the product, 4-methyl-3-nitroacetophenone, crystallizes, m.p. 61°–62° C.

Step B: Preparation of 3-amino-4-methylacetophenone

Hydrogenation of the nitroacetophenone in methanol (200 ml/100 mmoles nitro compound) over platinum oxide (0.1 g/1 g of nitro compound) gives the aniline derivative in excellent yield as a nearly colorless solid, m.p. 79°–80°.

Step C: Preparation of 2-(5-acetyl-2-methylphenylimino)imidazolidine

The aniline (3.58 g, 24 mmoles) is allowed to react with 10 mmoles (2.02 g) 2-chloroimidazoline bisulfate. The reaction is run and worked up substantially as described in Example 2 to furnish the 2-(5-acetyl-2-methylphenylimino)imidazolidine in 49% yield, m.p. 160°–162° C.

EXAMPLE 4

2-(4-Methoxycarbonyl-2-methylphenylimino)imidazolidine

Step A: Preparation of methyl 3-methyl-4-nitrobenzoate

3-Methyl-4-nitrobenzoic acid (67 g, 0.37 mole) is added to a mixture of dimethylacetamide (300 ml), iodomethane (85 g, 1.0 mole) and anhydrous sodium bicarbonate (84 g, 1.0 mole). The mixture is stirred and heated at reflux for two hours. The mixture is cooled, and filtered and the solids are washed with methanol before being discarded. The filtrate and washings are evaporated to a residue which crystallizes. Recrystallization from diethyl ether gives pure methyl 3-methyl-4-nitrobenzoate, 65.1 g, m.p. 73°–75.5° C.

Step B: Preparation of 4-methoxycarbonyl-2-methylaniline

The methyl ester (64 g) is hydrogenated in ethanol (500 ml) using 5% palladium on charcoal (2.0 g) as a catalyst until the theoretical amount of hydrogen is taken up. The catalyst is then filtered and washed with ethanol. The filtrate and washings are evaporated to a residue which crystallizes. Recrystallization from diethyl ether gives 61 g of 4-methoxycarbonyl-2-methylaniline, m.p. 168°–170° C.

Step C: Preparation of 2-(4-methoxycarbonyl-2-methylphenylimino)imidazolidine After reaction of the aniline from Step B with 2-chloro-2-imidazoline substantially as described in Example 2 there is isolated in 47% yield, 2-(4-methoxycarbonyl-2-methylphenylimino)imidazolidine, m.p. 193°–194.5° C.

EXAMPLE 5

2-(2-Chloro-4-diethylaminomethylphenylimino)imidazolidine

Step A: Preparation of 2-(2-chloro-4-methylphenylimino)-1,3-diacetylimidazolidine 2-(2-Chloro-4-methylphenylimino)imidazolidine (5.0 g) is heated at reflux for one hour in acetic anhydride (35 ml). The mixture is cooled, the remaining anhydride removed by distillation in vacuo and the residue partitioned between ice water and dichloromethane. The organic layer is washed with water to remove any residual acid, dried (Na$_2$SO$_4$), and evaporated to give crystalline 2-(2-chloro-4-methylphenylimino)-1,3-diacetylimidazolidine (5.43 g), which was used without further purification.

Step B: Preparation of 2-(2-chloro-4-bromomethylphenylimino)-1,3-diacetyliminoimidazolidine A 500 ml round bottom flask is charged with carbon tetrachloride (400 ml), the crystalline diacetate (5.0 g), N-bromosuccinimide (3.3 g, freshly recrystallized from water) and azobisisobutyronitrile (10 mg). The flask is illuminated with stirring to maintain solvent reflux. An additional portion (1.1 g) of N-bromosuccinimide is added after 30 minutes. After 1.5 hours the vessel is cooled and the solvent is removed in vacuo. The red residue is partitioned between water and dichloromethane and the organic phase is washed several times (3×250 ml) with water, dried and evaporated to a hard foam (7.2 g).

Step C: Preparation of 2-(2-chloro-4-diethylaminomethylphenylimino)imidazolidine A solution of the amorphous bromo derivative (1.12 g) in dichloromethane is added dropwise to diethylamine (1.5 ml, 14.5 mmoles) in dichloromethane (10 ml). After 15 minutes, the dark solution is concentrated to a residue and redissolved in methanol containing sodium methoxide (0.54 g, 10 mmoles). After 30 minutes, this solution is concentrated, diluted with ice water and extracted with dichloromethane. The extracts are pooled, evaporated to a residue and partitioned between diethyl ether and 2 N acetic acid. The layers are separated and the aqueous phase is washed with additional ether and concentrated slightly to remove dissolved ether. Charcoal treatment followed by careful addition of 50% sodium hydroxide gives several crops of crystals. The first crop is a multicomponent mixture but later crops are nearly pure product, 0.37 g, m.p. 113°–5°.

EXAMPLE 6

2-(2-Chloro-4-methoxymethylphenylimino)imidazolidine

The amorphous benzyl bromide derivative from Example 5, Step B (1.9 g) is dissolved in methanol (200 ml) and anhydrous potassium carbonate (9.0 g) is added and the mixture is stirred at reflux for two hours. The solids are filtered, washed with methanol and discarded. The filtrate is evaporated in vacuo to a residue which is purified by solution in dichloromethane and subjected to the extraction procedure substantially as described in Example 2. The crude solid which precipitates as the acidic extracts are basified, is recrystallized from toluene-hexane to give colorless crystals, of 2-(2-chloro-4-methoxymethylphenylimino)imidazolidine, 0.48 g, m.p. 108°–110°.

EXAMPLE 7

2-(2,6-Dimethyl-4-ethoxymethylphenylimino)imidazolidene

Step A: Preparation of 4-bromomethyl-2,6-dimethylnitrobenzene

Nitromesitylene (20.0 g) is added to a mixture of N-bromosuccinimide (11.7g, 2 equivalents) and azobisisobutyronitrile (10 mg) in carbon tetrachloride (1000 ml). The flask is illuminated with a bright incandescent bulb (controlled by a Variac) with stirring until reflux occurs; an additional heat source is required. After 4 hours the reaction mixture is cooled, evaporated to a residue and partitioned between water and dichloromethane. The organic phase is separated, dried, and evaporated to a residue which is purified by column chromatography on silica gel by gradient elution: benzene/hexane (1:9 to 4:1). The purified product, mostly 4-bromomethyl-2,6-dimethylnitrobenzene, is isolated as an orange oil, 36.8 g.

Step B: Preparation of 4-ethoxymethyl-2,6-dimethylnitrobenzene

The product from Step A (19.0 g) is dissolved in ethanol (600 ml) and anhydrous potassium carbonate (32 g) is added. The reaction mixture is stirred at reflux until the reaction is complete by tlc (two hours). The mixture is cooled, and the solids are filtered, washed, and discarded. The filtrate and washings are evaporated to a residue and purified by column chromatography on silica gel, using as eluant cyclohexane/ethyl acetate (97:3 v/v). The desired product, 4-ethoxymethyl-2,6-dimethylnitrobenzene (10.4 g) is isolated as a colorless oil.

Step C: Preparation of 4-ethoxymethyl-2,6-dimethylaniline

To a solution of the product from Step B (10.0 g) in 50% aqueous ethanol (150 ml) is added iron powder (7.5 g) and concentrated hydrochloric acid (2.0 ml in 10 ml ethanol). The mixture is stirred mechanically at reflux for 2 hours. The solids are filtered hot, washed with ethanol and discarded. The filtrate is neutralized with sodium bicarbonate, evaporated to a residue and extracted with dichloromethane. The organic phase is treated with charcoal and a small amount of silica gel, dried, and evaporated to afford crude, syrupy 4-ethoxymethyl-2,6-dimethylaniline. The product could be purified further by silica gel chromatography [cyclohexane/ethyl acetate (19:1)] or used directly in the next step. Yield after chromatography is 4.8 g.

Step D: Preparation of 2-(2,6-dimethyl-4-ethoxymethylphenylimino)imidazolidine

When the 4-ethoxymethylaniline derivative (2.4 g) is treated with 2-chloro-2-imidazoline in the manner described in Example 2, the title compound is obtained in good yield, 1.8 g, after crystallization from ether-hexane.

EXAMPLE 8

2-[4-(1-Hydroxyethyl)-2-methylphenylimino]imidazolidene

To a mixture of isopropanol (15 ml) and 0.5% sodium hydroxide in isopropanol (2.5 ml) is added sodium borohydride (92 mg, 2.4 mmoles) followed by a warm solution of 2-(4-acetyl-2-methylphenylimino)imidazolidine (0.5 g in 20 ml isopropanol). The mixture is stirred at 70° until the reaction is complete (6 hours). The mixture is diluted with water (50 ml) and 1 N sodium hydroxide (15 ml) and extracted several times with ethyl acetate. The combined extracts are backwashed with water, dried, and concentrated to a small volume. The remaining solvent is removed under high vacuum to give the product as a hard foam. Trituration with diethyl ether induces crystallization of the product (0.23 g), m.p. 133°–4°.

EXAMPLE 9

2-(2-Methyl-4-phenylthiophenylimino)imidazolidine

Step A: Preparation of 5-bromo-2-nitrotoluene

A solution of 4-bromotoluidine (27.9 g, 150 mmoles) in glacial acetic acid (600 ml) is stirred while 30% hydrogen peroxide (180 ml) and concentrated sulfuric acid (12 ml) are added. The mixture is heated in an oil bath at 100°. When the pot temperature reaches 65° the mixture darkens and there is a mild exotherm. The bath is removed and the temperature rises to 105°. When the reaction subsides, the bath is replaced and reflux is maintained for two hours. The mixture is cooled and poured onto ice (1500 g). The product crystallizes slowly with scratching. Another liter of cold water is added and the product is filtered and washed. The damp solid is dissolved in hexane, filtered, dried and evaporated to a residue which crystallizes to give 14.3 g of 5-bromo-2-nitrotoluene, containing minor contaminants by tlc [silica gel-dichloromethane/hexane (3:7)] which were removed by column chromatography using the same solvent system. Final weight; 12.8 g.

Step B: Preparation of 2-nitro-5-phenylthiotoluene

To a suspension of sodium hydride (57% oil emulsion, 1.11 g) in dimethylformamide (30 ml) is added in small portions 2.48 ml (2.64 g, 24 mmoles) of thiophenol. The mixture is cooled in an ice bath while a solution of 5-bromo-2-nitrotoluene (4.32 g, 20 mmoles) in dimethylformamide (10 ml) is added dropwise. The mixture is stirred for an additional 30 minutes and then poured into ice water (200 ml). The partially crystalline product is extracted with dichloromethane and the combined extracts are washed with water and dried. The solvents are evaporated under high vacuum to remove DMF and the residue is covered with hexane. The resultant crystals are broken up and filtered to give pure product, 2-nitro-5-phenylthiotoluene, 3.78 g, m.p. 69°–75°.

Step C: Preparation of 2-methyl-4-phenylthioaniline

A solution of the phenylthio derivative 2.0 g, 8.2 mmoles) in ethanol is added carefully to 5% palladium on charcoal (0.25 g) and hydrogenated (40 psi) until hydrogen uptake ceases. The catalyst is filtered and washed with methanol. The combined filtrate and washes are concentrated to a residue which is triturated with hexane to induce crystallization of 2-methyl-4-phenylthioaniline, 1.64 g, m.p. 64°–5°.

Step D: Preparation of 2-(2-methyl-4-phenylthiophenylimino)imidazolidine

The aniline derivative from Step C (3.0 g, 14 mmoles) is allowed to react with 2-chloro-2-imidazoline bisulfate (4.04 g, 20 mmoles) in methanol (60 ml) containing water (10 ml) and N,N-dimethylaniline (2.67 g, 22 mmoles). After 72 hours the reaction is worked up in the manner described in Example 2, except that the initial dichloromethane extracts are evaporated to a residue and triturated with hexane before extraction with 2 N acetic acid. The yield of pure product is 2.95 g, m.p. 140°–141° C.

Employing the procedure substantially as described in Example 9, but substituting for the thiophenol used in Step B thereof, an equimolecular amount of phenol, methylmercaptan or propylmercaptan, there are produced respectively:

2-(2-methyl-4-phenoxyphenylimino)imidazolidine;
2-(2-methyl-4-methylthiophenylimino)imidazolidine;
2-(2-methyl-4-propylthiophenylimino)imidazolidine, and
2-(2-methyl-4-ethylthiophenylimino)imidazolidine, m.p. 95°–96° C.

EXAMPLE 10

2-(4-Hydroxy-2-methylphenylimino)imidazolidine hydrobromide

A solution of 2-(4-methoxy-2-methylphenylimino)imidazolidine (2.05 g, 10 mmoles) in 48% hydrobromic acid (20 ml) is heated with stirring in an oil bath at 110°.

After six hours the solution is concentrated in vacuo to a residue that crystallizes. The difficultly soluble solid is dissolved in water, basified with 10% aqueous sodium bicarbonate, filtered and concentrated to a small volume whereupon the product crystallizes as the hydrobromide salt, 2.17 g, m.p. 215°–7°.

EXAMPLE 11

2-(4-Carboxy-2-methylphenylimino)imidazolidine hydrochloride 2-(4-Methoxycarbonyl-2-methylphenylimino)imidazolidine (2.0 g from Example 4) is dissolved in 4 N hydrochloric acid (30 ml) and heated at 75° C. for 18 hours. After cooling crystals separate which are filtered (2.2 g). Recrystallization from water gives 2-(4-carboxy-2-methylphenylimino)imidazolidine hydrochloride, m.p. 280°–281° C. (dec.).

EXAMPLE 12

2-(4-Carboxy-2,6-dimethylphenylimino)imidazolidine hydrochloride

Step A: Preparation of 4-methoxycarbonyl-3,5-dimethylaniline

Employing the procedure substantially as described in Example 4, Steps A and B but substituting for the 3-methyl-4-nitrobenzoic acid used as starting material in Step A, an equimolar amount of 3,5-dimethyl-4-nitrobenzoic acid, there is produced 4-methoxycarbonyl-2,6-dimethylaniline, m.p. 104°–106° C.

Step B: Preparation of 2-(4-methoxycarbonyl-2,6-dimethyl-phenylimino)imidazolidine Employing the procedure substantially as described in Example 2 but substituting for the 2-chloroaniline used therein an equimolecular amount of 4-methoxycarbonyl-3,5-dimethylaniline there is produced 2-(4-methoxycarbonyl-2,6-dimethylphenylimino)imidazolidine, m.p. 127°–129° C.

Step C: Preparation of 2-(4-carboxy-2,6-dimethylphenylimino)imidazolidine hydrochloride Employing the procedure substantially as described in Example 11, but substituting for the 2-(4-methoxycarbonyl-2-methylimino)imidazolidine used therein an equimolecular amount of 2-(4-ethoxycarbonyl-2,6-dimethylphenylimino)imidazolidine, there is produced 2-(4-carboxy-2,6-dimethylphenylimino)imidazolidine hydrochloride, m.p. 238–249 (dec.).

EXAMPLE 13

2-(4-Carboxy-2,6-dimethylphenylimino)imidazolidine 2-(2,4,6-Trimethylphenylimino)imidazolidine (2.03 g) is dissolved in glacial acetic acid (50 ml) and cooled as 5.0 g of chromium trioxide is added in small portions. The solution is then heated to 50° in an oil bath for 4 hours when the reaction is complete as shown by tlc [silica gel, EtOAc/iPA/2 N NH4OH (2:5:1 v/v/v). The mixture is poured into water and ice (500 ml) and the resultant precipitate is filtered and washed with water. Recrystallization from ethyl acetate gives pure product, m.p. 116°–117° C. (1.35 g, 76%).

EXAMPLE 14

2-(3-Diethylamino-2-methyl)imidazolidine

Peracetylated 2-(2-methyl-3-nitrophenylimino)imidazolidine (prepared from unacetylated precursor (1.1 g, 0.005 mole) by the method of Example 5, Step A) is dissolved in ethanol (50 ml) and excess acetaldehyde is added (5 ml). Platinum oxide (150 mg) is added and the mixture is hydrogenated at atmospheric pressure until there is no further change in the thin layer chromatogram of the mixture. The major product is the diethylamino derivative which is purified by preparative layer chromatography and deacetylated by the procedure described in Example 5, Step C using sodium methoxide in methanol or potassium carbonate in methanol to give the desired product. After purification by preparative layer chromatography with ethyl acetate:2-propanol:2 N NH4OH (2:5:1 v/v/v) and crystallization from toluene-hexane there is obtained 0.185 g (15%) of 2-(3-diethylamino-2-methyl)imidazolidine, m.p. 107°–111° (dec.).

EXAMPLE 15

2-(2-Chloro-4-ethenylphenylimino)imidazolidine

Step A: Preparation of 2-(2-chloro-4-formylphenylimino)-1,3-diacetylimidazolidine A solution of 2-(2-chloro-4-bromomethylphenylimino)-1,3-diacetyliminoimidazolidine (1.67 g) in DMSO (25 ml) is stirred under nitrogen at 60° C. for 3 hours. Ice water is added, the mixture is filtered, and the precipitate is washed with water and hexane. The filtrate and washes are extracted with ethyl acetate (3×100 ml) and the extracts are combined and added to the precipitate to dissolve it. The solution is washed with saturated salt solution, dried over sodium sulfate and evaporated to a residue (0.775 g) which contains one major component by tlc and shows a strong aldehyde proton in the nmr.

Step B: Preparation of 2-(2-chloro-4-ethenylphenylimino)imidazolidine

Sodium hydride dispersion (57%, 42 mg) is washed with petroleum ether (3×) by decantation and then DMSO (2 ml) is added under nitrogen. The mixture is heated briefly at 70° C. to effect solution. When the foaming stops the solution is allowed to cool and triphenylphosphonium bromide (0.357 g, 0.001 mole) is added. The solution is stirred for 30 minutes. The aldehyde derivative (0.22 g) from Step A is added in DMSO (1 ml) dropwise. After stirring for 18 hours, the solution is diluted with ice water and extracted with ethyl acetate (3×5 ml). The extracts are combined, washed with saturated salt solution, dried over sodium sulfate and evaporated in vacuo to a residue (0.305 g). Purification by preparative layer chromatography gives the acetylated styryliminoimidazolidine derivative as a viscous oil (0.105 g). Deacetylation with catalytic methoxide in methanol at ambient temperature gives 0.065 g of 2-(2-chloro-4-ethenylphenylimino)imidazolidine as a colorless solid after crystallization from dichloromethane-cyclohexane, m.p. 98°–101° C.

EXAMPLE 16

2-(2-Ethenyl-3-methoxy-phenylimino)imidazolidine

Step A: Preparation of 2-(2-hydroxyethyl)-3-pivalamidoanisole

To N-pivaloylanisidine (4.14 g, 0.02 mole) in freshly distilled THF (60 ml) under nitrogen is added 2.3 N butyllithium in hexane (23 ml) at 0° C. and the resultant solution is stirred at 0° C. for 2 hours. Ethylene oxide (liquid, 1.6 ml) is added and the reaction mixture is stirred for an hour at 0° C. and then an additional hour at ambient temperature. Acetic acid (2 ml) and water (30 ml) are added to quench the reaction. The THF is evaporated in vacuo and the aqueous mixture is extracted with ether (2×30 ml). The extracts are combined, washed with 5% sodium bicarbonate solution, brine, dried over sodium sulfate and concentrated to 5.42 g of crystalline material. Recrystallization from n-butyl chloride (13 ml) gives 3.46 g (69%) of 2-(2-hydroxyethyl)-3-pivalamidoanisole, m.p. 118°–119.5° C.

Step B: Preparation of 2-ethenyl-m-anisidine

Treatment of 2-(2-hydroxyethyl)-3-pivalamidoanisole with pyridine/thionyl chloride by the method of Example 18 gives an 83% yield of the dehydration product, 2-pivalamido-6-methoxystyrene as a crude solid. Dissolution of the pivalamido derivative (2.3 g) in methanol containing a catalytic amount of sodium methoxide and stirring for 18 hours removes the pivalamido group. Neutralization with solid $CO_2$ and evaporation gives an oil which is distilled to furnish the pure 2-ethenyl-m-anisidine (bp.=120°–135° C., 10 mm, 0.85 g, 57%).

Step C: Preparation of 2-(2-ethenyl-3-methoxy-phenylimino)imidazolidine

Reaction of the 2-ethenyl-m-anisidine with 2-chloroimidazoline by the method described in Example 2 gives a 47% yield of 2-(2-ethenyl-3-methoxy-phenylimino)imidazolidine, m.p. 125.5°–126° C.

EXAMPLE 17

2-[2-ethenylphenylimino]imidazolidine

Step A: Preparation of N'-Tosyl-2-(phenylimino)imidazolidine 2-(Phenylimino)imidazolidine (0.773 g, 4.8 mmoles) is dissolved in dry THF (15 ml), cooled to −78° C. under nitrogen protected from moisture and 2.4 N butyllithium in hexane (2.0 ml) is added. Then p-toluenesulfonyl chloride (0.953 g, 5 mmoles) in THF (3 ml) at −78° C. is added. The mixture is stirred for 90 minutes and allowed to warm to ambient temperature. The volatiles are evaporated in vacuo and water and ether are added. Crystals separate in the ether layer which are filtered and recrystallized from isopropanol to remove some bistosyl derivative. The major product, confirmed by n.m.r is N'-Tosyl-2-(phenylimino)imidazolidine, (610 mg, 40%), m.p. 174°–177° C.

Step B: Preparation of N'-tosyl-2-[2-(2-hydroxyethylphenylimino]imidazolidine Hydroxyethylation of N'-tosyl-2-(phenylimino)imidazolidine with ethylene oxide by the same procedure described in Example 16 gives a 55% yield of crystalline N-tosyl- product, m.p. 185° C.

Step C: Preparation of 2-(2-ethenylphenylimino)imidazolidine

N'-Tosyl-2-[2-(2-hydroxyethyl)-phenylimino]imidazolidine from Example 17, Step B (1.8 g) is dissolved in pyridine (25 ml) containing thionyl chloride (3 ml). The mixture is heated at reflux until thin layer chromatography shows starting material to be gone [silica gel=dichloromethane:methanol (19:1)], about three hours. The volatiles are evaporated in vacuo and the residue is partitioned between water and ether. The aqueous layer is extracted (3×50 ml) with ether and the combined extracts are washed with brine, dried over sodium sulfate and evaporated to off white crystals which can be purified by recrystallization from ethyl acetate (1.23 g, 72%). Ammonia (50 ml) is condensed in a cooled flask fitted with a dry ice condenser. The N-tosyl derivative (0.5 g) is added and when solution occurs, small pieces of freshly cut metallic sodium are added one at a time until a blue color persists. Solid ammonium chloride is added to remove the blue color and the ammonia is evaporated in a stream of nitrogen. The solid residue is partitioned between water and ether. The aqueous layer is basified to pH 14 and reextracted with dichloromethane (2×50 ml). The organic extracts are pooled, extracted with 2 N acetic acid (3×50 ml) and these extracts are combined, back-extracted with dichloromethane, and neutralized with dilute hydrochloric acid.

The product crystallizes and is collected and recrystallized from toluene/hexane to furnish 41% yield of product; m.p. 111°–112° C.

EXAMPLE 18

Anovulatory Activity—(EPI)

Prime laying hens (7–12 months), whose egg production has been documented during the preceding 2 weeks, are fed diet containing medication at 100 ppm for 8 days. Egg production is recorded for days 5 through 8 while the birds are on test, and the Egg Production Index (EPI) is calculated as the % of control egg production for days 5 through 8 inclusive after start of oral medication at 100 ppm. The results are shown in Table I.

EXAMPLE 19

Antigonadal Activity—($ED_{20}$)

Prime laying hens (7–12 months), whose egg production has been documented during the preceding 2 weeks, are fed medicated diet for one week at various dose levels. At the conclusion of the one week test, the hens are sacrificed and their reproductive system is excised, examined and weighed. The seven day medication level producing a 20 g ovarian weight, based on at least 8 hens at 2 dose levels is calculated and recorded as $ED_{20}$. The results are shown in Table I.

TABLE I

AVIAN ANOVULATORY AND ANTIGONADAL ACTIVITIES OF CERTAIN 2-(PHENYL IMINO)IMIDAZOLIDINES

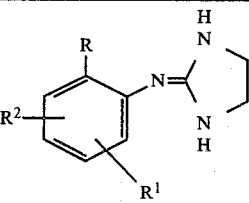

| | Anovulatory Activity (Hens) | |
|---|---|---|
| R, $R^1$, $R^2$ | $ED_{20}$ (ppm)* | EPI (%)** |
| 1. 2,6-Dimethyl | 38 | 18 |
| 2. 2-Methyl, 3-Chloro | 38 | 26 |
| 3. 2-Methyl, 6-Chloro | 40 | 16 |
| 4. 2,4-Dimethyl | 50 | 24 |
| 5. 2-Methyl, 4-Chloro | 53 | 24 |
| 6. 2,4,6-Trimethyl | 54 | 31 |
| 7. 2-Methyl, 4-Bromo | 56 | 24 |
| 8. 2-Methyl, 5-Fluoro | 67 | 24 |
| 9. 2-Methyl | 69 | 8 |
| 10. 2-Ethyl | 83 | 31 |
| 11. 2,6-Diethyl | 151 | 31 |
| 12. 2,3-Dimethyl | 181 | 86 |
| 13. 2-Chloro | 217 | 31 |
| 14. 2,5-Dimethyl | 250 | 70 |
| 15. 2,6-Dichloro | 400 | 70 |

*Seven day medication level producing a 20 g ovarian weight in laying hens (based on at least 8 hens at 2 dose levels)
**Egg Production Index, % of control egg production for days 5 through 8 inclusive after start of oral medication at 100 ppm

What is claimed is:

1. An anovulatory composition comprising a solid poultry feedstuff having intimately dispersed therein at least an effective anovulatory amount of a compound of structural formula:

or a non-toxic salt thereof, wherein:
R is
(1) $C_{1-4}$ alkyl,
(2) $C_{2-5}$ alkenyl,
(3) chloro,
(4) bromo, or
(5) iodo;
$R^1$ and $R^2$ are independently
(1) $C_{1-4}$ alkyl,
(2) $C_{2-5}$ alkenyl,
(3) chloro,
(4) fluoro,
(5) bromo,
(6) iodo,
(7) hydrogen,
(8) nitro,
(9) amino,
(10) $C_{1-3}$ alkylamino,
(11) di($C_{1-3}$ alkyl)amino,
(12) hydroxy,
(13) carboxy,
(14) $C_{1-3}$ alkoxycarbonyl,
(15) $C_{1-4}$ alkanoyl,
(16) $C_{1-4}$ alkylthio,
(17) trifluoromethylthio,
(18) phenylthio,
(19) $C_{1-3}$ alkylphenylthio
(20) $C_{1-3}$ alkoxyphenylthio
(21) chlorophenylthio,
(22) bromophenylthio,
(23) phenoxy,
(24) $C_{1-3}$ alkylphenoxy,
(25) $C_{1-3}$ alkoxyphenoxy,
(26) chlorophenoxy,
(27) bromophenoxy,
(28) amino-$C_{1-4}$ alkyl,
(29) $C_{1-3}$ alkylamino-$C_{1-4}$ alkyl,
(30) di($C_{1-3}$ alkyl)amino-$C_{1-4}$ alkyl,
(31) hydroxy $C_{1-4}$ alkyl, or
(32) $C_{1-3}$ alkoxy-$C_{1-4}$ alkyl.

2. The anovulatory composition of claim 1 wherein R is $C_{1-4}$ alkyl, one of $R^1$ and $R^2$ is hydrogen, and the other is $C_{1-4}$ alkyl, fluoro, chloro, or $C_{1-3}$ alkoxy-$C_{1-4}$ alkyl.

3. The anovulatory composition of claim 2 wherein the anovulatory compound is:
2-(2,6-dimethylphenylimino)imidazolidine,
2-(3-chloro-2-methylphenylimino)imidazolidine,
2-(6-chloro-2-methylphenylimino)imidazolidine,
2-(2-methyl-4-methoxymethylphenylimino) imidazolidine, or
2-(5-fluoro-2-methylphenylimino)imidazolidine
or a non-toxic salt thereof.

4. The composition of claim 1, 2, or 3 wherein the anovulatory compound comprises from about 20 to about 500 parts per million by weight.

5. The composition of claim 2 or 3 wherein the anovulatory compound comprises from about 30 to about 250 parts per million by weight.

6. A poultry feed premix composition comprising a solid poultry feedstuff having intimately dispersed therein an anovulatory compound in sufficient amount so that after dilution to final poultry feed said feed contains an effective amount of the anovulatory compound of structural formula:

or a non-toxic salt thereof, wherein:
R is
(1) $C_{1-4}$ alkyl,
(2) $C_{2-5}$ alkenyl,
(3) chloro,
(4) bromo, or
(5) iodo;
$R^1$ and $R^2$ are independently
(1) $C_{1-4}$ alkyl,
(2) $C_{2-5}$ alkenyl,
(3) chloro,
(4) fluoro,
(5) bromo,
(6) iodo,
(7) hydrogen,
(8) nitro,
(9) amino,
(10) $C_{1-3}$ alkylamino,
(11) di($C_{1-3}$ alkyl)amino,
(12) hydroxy,
(13) carboxy,
(14) $C_{1-3}$ alkoxycarbonyl,
(15) $C_{1-4}$ alkanoyl,
(16) $C_{1-4}$ alkylthio,
(17) trifluoromethylthio,
(18) phenylthio,
(19) $C_{1-3}$ alkylphenylthio
(20) $C_{1-3}$ alkoxyphenylthio
(21) chlorophenylthio,
(22) bromophenylthio,
(23) phenoxy,
(24) $C_{1-3}$ alkylphenoxy,
(25) $C_{1-3}$ alkoxyphenoxy,
(26) chlorophenoxy,
(27) bromophenoxy,
(28) amino-$C_{1-4}$ alkyl,
(29) $C_{1-3}$alkylamino-$C_{1-4}$alkyl,
(30) di($C_{1-3}$alkyl)amino-$C_{1-4}$alkyl,
(31) hydroxy $C_{1-4}$alkyl, or
(32) $C_{1-3}$alkoxy-$C_{1-4}$alkyl.

7. The poultry feed premix of claim 6 wherein R is $C_{1-4}$ alkyl, one of $R^1$ and $R^2$ is hydrogen, and the other is $C_{1-4}$ alkyl, fluoro, chloro, or $C_{1-3}$ alkoxy-$C_{1-4}$ alkyl.

8. The poultry feed premix of claim 7, wherein the anovulatory compound is:
2-(2,6-dimethylphenylimino)imidazolidine,
2-(3-chloro-2-methylphenylimino)imidazolidine, 2-(6-chloro-2-methylphenylimino)imidazolidine,
2-(2-methyl-4-methoxymethylphenylimino)imidazolidine, or
2-(5-fluoro-2-methylphenylimino)imidazolidine
or a non-toxic salt thereof.

9. The poultry feed premix of claim 6, 7 or 8 wherein the anovulatory agent comprises about 2 to about 50% by weight of the composition.

10. The poultry feed premix of claim 6, 7 or 8 wherein the anovulatory agent comprises about 5 to about 25% by weight of the composition.

11. A method of arresting ovulation in poultry which comprises the administration to the poultry of an effective amount of an anovulatory compound of formula:

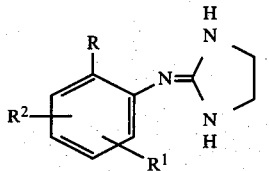

or a non-toxic salt thereof, wherein:
R is
   (1) $C_{1-4}$alkyl,
   (2) $C_{2-5}$alkenyl,
   (3) chloro,
   (4) bromo, or
   (5) iodo;
$R^1$ and $R^2$ are independently
   (1) $C_{1-4}$alkyl,
   (2) $C_{2-5}$alkenyl,
   (3) chloro,
   (4) fluoro,
   (5) bromo,
   (6) iodo,
   (7) hydrogen,
   (8) nitro,
   (9) amino,
   (10) $C_{1-3}$alkylamino,
   (11) di($C_{1-3}$alkyl)amino,
   (12) hydroxy,
   (13) carboxy,
   (14) $C_{1-3}$alkoxycarbonyl,
   (15) $C_{1-4}$alkanoyl,
   (16) $C_{1-4}$alkylthio,
   (17) trifluoromethylthio,
   (18) phenylthio,
   (19) $C_{1-3}$alkylphenylthio,
   (20) $C_{1-3}$alkoxyphenylthio,
   (21) chlorophenylthio,
   (22) bromophenylthio,
   (23) phenoxy,
   (24) $C_{1-3}$alkylphenoxy,
   (25) $C_{1-3}$alkoxyphenoxy,
   (26) chlorophenoxy,
   (27) bromophenoxy,
   (28) amino-$C_{1-4}$alkyl,
   (29) $C_{1-3}$alkylamino-$C_{1-4}$alkyl,
   (30) di($C_{1-3}$alkyl)amino-$C_{1-4}$alkyl,
   (31) hydroxy $C_{1-4}$alkyl, or
   (32) $C_{1-3}$alkoxy-$C_{1-4}$alkyl.

12. The method of claim 11 wherein R is $C_{1-4}$ alkyl, one of $R^1$ and $R^2$ is hydrogen, and the other is $C_{1-4}$ alkyl, fluoro, chloro, or $C_{1-3}$ alkoxy-$C_{1-4}$ alkyl.

13. The method of claim 12 wherein the anovulatory compound is:
2-(2,6-dimethylphenylimino)imidazolidine,
2-(3-chloro-2-methylphenylimino)imidazolidine,
2-(6-chloro-2-methylphenylimino)imidazolidine,
2-(2-methyl-4-methoxymethylphenylimino)imidazolidine, or
2-(5-fluoro-2-methylphenylimino)imidazolidine
or a non-toxic salt thereof.

14. The method of claim 11, 12 or 13 wherein the compound is administered orally as a component of the poultry feed, comprising from about 20 to about 500 parts per million by weight of the feed.

15. The method of claim 11, 12 or 13 wherein the compound is administered orally as a component of the poultry feed comprising from about 30 to about 250 parts per million by weight of the feed.

16. The method of claim 11, 12 or 13 wherein the compound or non-toxic salt thereof is administered orally as a component of drinking water comprising about 25 to about 100 parts per million by weight of the water.

17. The method of claim 11, 12 or 13 wherein the compound or non-toxic salt thereof is administered orally as a component of drinking water comprising about 25 to about 100 parts per million by weight of the water.

18. The method of claim 17 wherein the non-toxic salt is the hydrochloride.

* * * * *